US011399767B2

(12) United States Patent
Youm et al.

(10) Patent No.: US 11,399,767 B2
(45) Date of Patent: Aug. 2, 2022

(54) BIO-STIMULATING AND BIO-SIGNAL MEASURING CIRCUIT

(71) Applicant: ELECTRONICS AND TELECOMMUNICATIONS RESEARCH INSTITUTE, Daejeon (KR)

(72) Inventors: WooSub Youm, Daejeon (KR); Sung Q Lee, Daejeon (KR); Gunn Hwang, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 334 days.

(21) Appl. No.: 16/513,468

(22) Filed: Jul. 16, 2019

(65) Prior Publication Data
US 2019/0336070 A1    Nov. 7, 2019

Related U.S. Application Data

(62) Division of application No. 15/424,477, filed on Feb. 3, 2017, now Pat. No. 10,390,756.

(30) Foreign Application Priority Data

Feb. 22, 2016    (KR) .......................... 10-2016-0020728

(51) Int. Cl.
*A61B 5/00* (2006.01)
*A61N 1/20* (2006.01)
(Continued)

(52) U.S. Cl.
CPC .............. *A61B 5/4836* (2013.01); *A61N 1/20* (2013.01); *A61N 1/36014* (2013.01);
(Continued)

(58) Field of Classification Search
CPC ....... A61B 5/4836; A61B 5/398; A61B 5/369; A61B 5/318; A61B 5/389; A61N 1/20;
(Continued)

(56) References Cited

U.S. PATENT DOCUMENTS 4,979,507 A    12/1990    Heinz et al.
5,620,474 A     4/1997    Koopman
(Continued)

FOREIGN PATENT DOCUMENTS

EP          0627241 A2    12/1994
KR    1020140116657 A    10/2014
KR       101566786 B1    11/2015

*Primary Examiner* — Tammie K Marlen (57) ABSTRACT

The circuit for measuring a bio-stimulating and bio-signal according to an embodiment of the inventive concept may include a bio-stimulating signal generating circuit, a bio-signal electrode, a switch block, first and second resistors, and a bio-signal measuring circuit. The bio-stimulating signal generating circuit may generate a bio-stimulating signal in a bio-stimulating mode. The bio-signal electrode may to deliver the bio-stimulating signal generated in the bio-stimulating mode and receive a bio-signal in a bio-signal measuring mode. The switch block may be turned on in a case where a voltage of the bio-stimulating signal is greater than a first reference voltage or lower than a second reference voltage. The first and second resistors may be serially connected between the bio-signal electrode and the switch block and divide a voltage of a signal of the bio-signal electrode according to whether the switch block is turned on. The bio-signal measuring circuit may measure voltage signals divided by the first and second resistors or measure a signal of the bio-signal electrode, according to whether the switch block is turned on. The first reference voltage may be greater than the second reference voltage.

5 Claims, 7 Drawing Sheets

(51) Int. Cl.
    *A61N 1/36*     (2006.01)
    *A61B 5/318*     (2021.01)
    *A61B 5/369*     (2021.01)
    *A61B 5/389*     (2021.01)
    *A61B 5/398*     (2021.01)

(52) U.S. Cl.
    CPC ............... *A61B 5/318* (2021.01); *A61B 5/369* (2021.01); *A61B 5/389* (2021.01); *A61B 5/398* (2021.01)

(58) Field of Classification Search
    CPC ...... A61N 1/36014; A61N 1/025; A61N 1/08; A61N 1/36125; A61N 1/3704; A61N 1/3912
    See application file for complete search history.

(56) References Cited

U.S. PATENT DOCUMENTS

| | | |
|---|---|---|
| 8,649,853 B2 | 2/2014 | Sweeney et al. |
| 8,892,206 B1 | 11/2014 | Swanson |
| 2002/0022867 A1 | 2/2002 | Akiyama et al. |
| 2010/0114248 A1* | 5/2010 | Donofrio ............ A61N 1/39624 607/60 |
| 2010/0185076 A1 | 7/2010 | Jeong et al. |
| 2010/0204766 A1* | 8/2010 | Zdeblick ................ A61N 1/056 607/119 |
| 2013/0197338 A1 | 8/2013 | Yu et al. |

\* cited by examiner

BIO-STIMULATING AND BIO-SIGNAL MEASURING CIRCUIT

CROSS-REFERENCE TO RELATED APPLICATIONS

This application is a divisional of U.S. Non-Provisional patent application Ser. No. 15/424,477, filed Feb. 3, 2017 which claims priority under 35 U.S.C. § 119 of Korean Patent Application No. 10-2016-0020728, filed on Feb. 22, 2016, the entire contents of which are hereby incorporated by reference.

BACKGROUND

The present disclosure herein relates to an implantable medical device, and more particularly, to a bio-stimulating and bio-signal measuring circuit.

With development in a low-power, high-density electronic circuit implementation technology and a high energy density battery technology, an implantable medical device has decreased in size, has multi-function, and has multi-channel. A deep brain stimulator or defibrillator is an example of a commercialized implantable medical device. Also, the commercialization of various implantable medical devices is in progress, such as a stomach stimulator, a foot drop treatment device, cochlear implantation, and brain computer interface (BCI) or an implantable drug pump.

The implantable medical devices are different in symptoms to be treated while most of them have the same algorithm. When an abnormal state in a corresponding bio-signal according to the symptom to be treated is detected, the implantable medical device stimulates the nerve of a specific part. The implantable medical device relieves or removes the symptom to be treated by such a stimulation signal, and allows a corresponding bio-signal to become normal.

However, in an existing implantable medical device, a bio-stimulating mode and a bio-signal measuring mode are divided. The reason is to prevent a bio-signal signal measuring circuit from becoming damaged by a bio-stimulating signal. Thus, the existing implantable medical device cannot simultaneously perform the bio-stimulating mode and the bio-signal measuring mode. Thus, the existing implantable medical device has a limitation in that it is difficult to handle an abnormal signal in real time that may be caused upon the application of the bio-stimulating signal.

SUMMARY

The present disclosure provides a bio-stimulating and bio-signal measuring circuit that automatically protects a bio-signal measuring circuit in a bio-stimulating mode and simultaneously performs bio-stimulating and bio-signal measurement with a single electrode.

An embodiment of the inventive concept provides a bio-stimulating and bio-signal measuring circuit including a bio-stimulating signal generating circuit, a bio-signal electrode, a switch block, first and second resistors, and a bio-signal measuring circuit. The bio-stimulating signal generating circuit may generate a bio-stimulating signal in a bio-stimulating mode. The bio-signal electrode may to deliver the bio-stimulating signal generated in the bio-stimulating mode and receive a bio-signal in a bio-signal measuring mode. The switch block may be turned on in a case where a voltage of the bio-stimulating signal is greater than a first reference voltage or lower than a second reference voltage. The first and second resistors may be serially connected between the bio-signal electrode and the switch block and divide a voltage of a signal of the bio-signal electrode according to whether the switch block is turned on. The bio-signal measuring circuit may measure voltage signals divided by the first and second resistors or measure a signal of the bio-signal electrode, according to whether the switch block is turned on. The first reference voltage may be greater than the second reference voltage.

In an embodiment of the inventive concept, a circuit for measuring a bio-stimulating signal and a bio-signal includes a bio-stimulating signal generating circuit, a multiplexer, a connection node, a switch block, first and second serially connected resistors, and a bio-signal measuring circuit. The bio-stimulating signal generating circuit may generate a bio-stimulating signal in a bio-stimulating mode. The first and second bio-signal electrodes may output the bio-stimulating signal generated in the bio-stimulating mode and receive a bio-signal in a bio-signal measuring mode. The multiplexer may select at least one of the first and second bio-signal electrodes by a control signal and connect the selected bio-signal electrode to the bio-stimulating signal generating circuit. The connection node may allow the bio-stimulating signal generating circuit and the multiplexer to be connected thereto. The switch block may be turned on in a case where a voltage of the bio-stimulating signal is greater than a first reference voltage or lower than a second reference voltage. The first and second serially connected resistors may be connected between the connection node and the switch block and divide a voltage of a signal of the selected bio-signal electrode according to whether the switch block is turned on. The bio-signal measuring circuit may measure voltage signals divided by the first and second resistors or measure a signal of the selected bio-signal electrode, according to whether the switch block is turned on. The first reference voltage may be greater than the second reference voltage.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

It should be understood that the foregoing general descriptions and the following detailed descriptions are all exemplary, and it should be appreciated that the additional descriptions of the claimed invention are provided. Reference signs are shown in detail in the exemplary embodiments of the inventive concept, and their examples are shown in reference drawings. Wherever possible, the same reference numeral is used for descriptions and drawings in order to refer to the same or similar part.

In the following, a semiconductor circuit would be used as an example for describing the characteristic and function of the inventive concept. However, a person skilled in the art would be capable of easily understanding other advantages and performance of the inventive concept according to the content set forth herein. The inventive concept would also be capable of being implemented or applied through other embodiments. Moreover, the detailed description may be modified or changed according to a perspective and application without departing significantly from the scope, technical spirit and other objects of the inventive concept.

Figure 1:
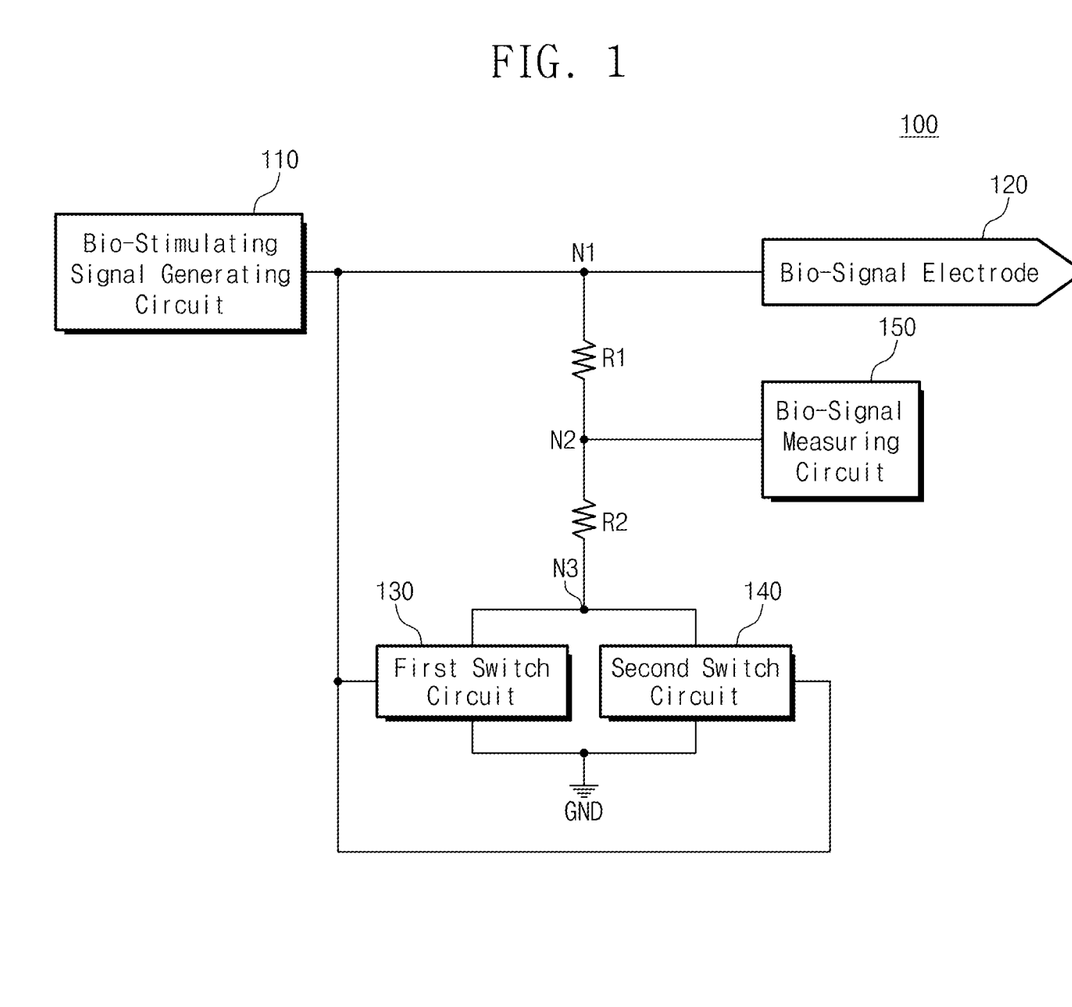
FIG. 1 is a circuit diagram that shows a bio-stimulating and bio-signal measuring circuit according to an embodiment of the present application.

FIG. 1 is a circuit diagram that shows a bio-stimulating and bio-signal measuring circuit according to an embodiment of the present application. Referring to FIG. 1, the bio-stimulating and bio-signal measuring circuit 100 may include a bio-stimulating signal generating circuit 110, a bio-signal electrode 120, first and second resistors R1 and R2, first and second switch circuits 130 and 140, and a bio-signal measuring circuit 150.

The operation of the bio-stimulating and bio-signal measuring circuit 100 may be divided into a bio-stimulating mode and a bio-signal measuring mode. The bio-stimulating mode is a mode in which the bio-stimulating and bio-signal measuring circuit 100 stimulates a body. The bio-signal measuring mode is a mode in which the bio-stimulating and bio-signal measuring circuit 100 measures a response signal for a bio-stimulating signal or a general bio-signal from a body.

The bio-stimulating signal generating circuit 110 is connected to the bio-signal electrode 120, the first resistor R1, and the first and second switch circuits 130 and 140 through the first node N1. The bio-stimulating signal generating circuit 110 generates a bio-stimulating signal in the bio-stimulating mode. The generated bio-stimulating signal is provided to the bio-signal electrode 120. Also, the generated bio-stimulating signal is provided to the first and second switch circuits 130 and 140. For example, the bio-stimulating signal may be a voltage or current signal. Thus, the bio-stimulating signal generating circuit 110 may include all circuits that may generate the voltage or current signal. For example, the bio-stimulating signal generating circuit 110 may include a digital analog converter (DAC) or function generator.

For example, the bio-stimulating signal may include at least one of transcranial Direct Current Stimulation (tDCS), transcranial Alternating Current Stimulation (tACS), or transcranial Random-Noise Stimulation (tRNS).

The bio-signal electrode 120 is connected to the bio-stimulating signal generating circuit 110, the first resistor R1, and the first and second switch circuits 130 and 140 through the first node N1. The bio-signal electrode 120 delivers to a body the bio-stimulating signal generated by the bio-stimulating signal generating circuit 110. Alternatively, the bio-signal electrode 120 receives the bio-signal from the body. That is, the bio-signal electrode 120 may be used for both bio-stimulating signal generation and bio-signal measurement.

For example, the bio-signal may include at least one of electroencephalogram (EEG), electrocardiogram (ECG), electromyogram (EMG), or electrooculography (EOG).

The first resistor R1 is connected between the first node N1 and the second node N2. The second resistor R2 is connected between the second node N2 and a third node N3. In the case where at least one of the first and second switch circuits 130 and 140 is turned on, the first and second resistors R1 and R2 may operate as voltage dividers. In this case, the first and second resistors R1 and R2 divide a voltage of the first node according to the proportion of values of the first resistor R1 and the second resistor R2 to provide the voltage to the second node N2.

For example, resistances of the first resistor R1 and the second resistor R2 may be determined so that the amount of current flowing along the first resistor R1 is lower than an allowable amount of current of the bio-signal measuring circuit 150. Alternatively, the resistances of the first resistor R1 and the second resistor R2 may be determined to be lower than the allowable amount of current of the first and second switch circuits 130 and 140. Also, the proportion of the resistances of the first resistor R1 and the second resistor R2 may be defined by an allowable range of voltage of the bio-signal measuring circuit 150. That is, the first and second resistors R1 and R2 are circuits for preventing the bio-signal measuring circuit 150 from becoming damaged by a bio-stimulating signal.

The first and second switch circuits 130 and 140 are connected between the third node N3 and a first source voltage GND. The first switch circuit 130 may be set to be turned on in the case where a voltage is equal to or higher than a first reference voltage Vref1. The second switch circuit 140 may be set to be turned on in the case where a voltage is equal to or lower than a second reference voltage Vref2. In the present embodiment, the first and second switch circuits 130 and 140 are controlled by a voltage of the first node N1. Here, the voltage of the first node N1 would be a bio-stimulating signal or bio-signal as described above. Thus, the first switch circuit 130 is turned on in the case where the voltage of the first node N1 is equal to or higher than the first reference voltage Vref1. The second switch circuit 140 is turned on in the case where the voltage of the first node N1 is lower than or equal to the second reference voltage Vref2. The first reference voltage Vref1 is greater than the second reference voltage Vref2. The conditions and examples of the first and second reference voltages Vref1 and Vref2 would be described with reference to FIG. 2.

For example, the first switch circuit 130 may include an NMOS transistor. In this case, the first reference voltage Vref1 would be the threshold voltage of the NMOS transistor. Alternatively, the first switch circuit 130 may include an NPN type bipolar junction transistor (BJT). For example, the second switch circuit 140 may include a PMOS transistor. In this case, the second reference voltage Vref2 would be the threshold voltage of the PMOS transistor. Alternatively, the second switch circuit 140 may include a PNP type BJT. The operating regions of the first and second switch circuits 130 and 140 according to the voltage of the first node N1 would be described with reference to FIG. 2.

Figure 2:
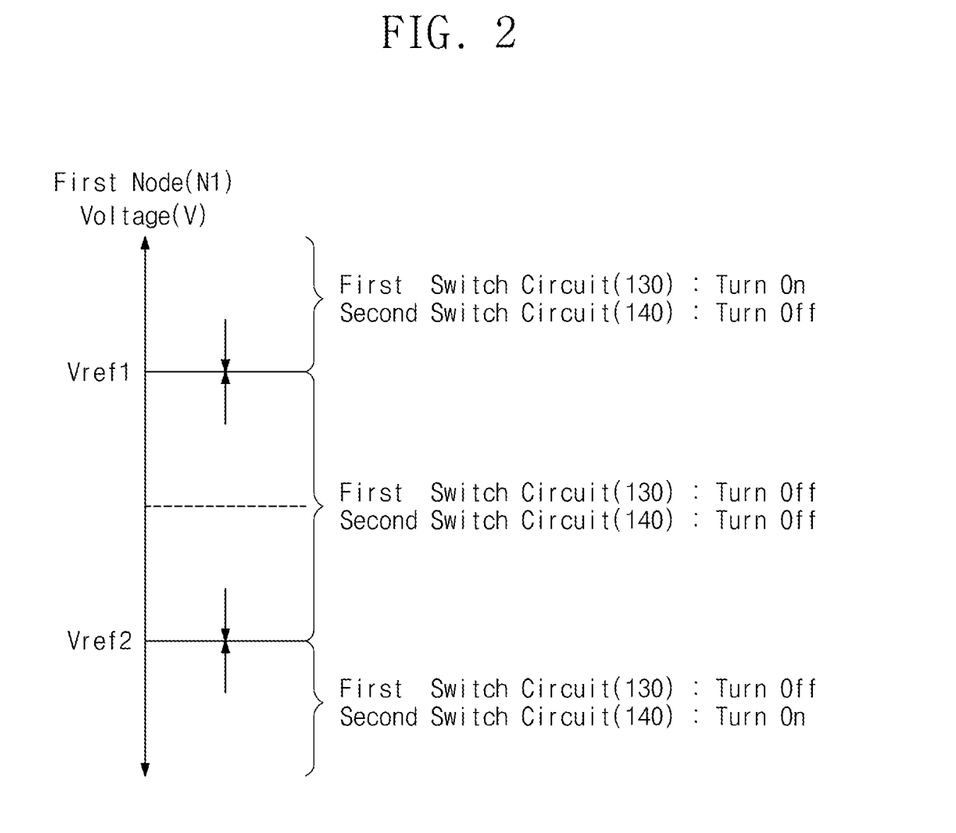
FIG. 2 is a conceptual diagram that shows operations according to the voltages of first nodes of first and second switch circuits shown in FIG. 1.

FIG. 2 is a conceptual diagram that shows operations according to the voltages of first nodes of first and second switch circuits shown in FIG. 1. Referring to FIG. 2, it is possible to be aware of the operating states of the first and second switch circuits 130 and 140 in FIG. 1 according to a level of a bio-stimulating signal.

In the case where a voltage of the first node N1 is greater than the first reference voltage Vref1, the first switch circuit 130 is turned on and the second switch circuit 140 is turned off. In the case where the voltage of the first node N1 is a voltage level between the first reference voltage Vref1 and the second reference voltage Vref2, the first and second switch circuits 130 and 140 are turned off. In the case where the voltage of the first node N1 is lower than the second reference voltage Vref2, the first switch circuit 130 is turned off and the second switch circuit 140 is turned on.

The first and second switch circuits 130 and 140 are circuits for preventing the bio-signal measuring circuit 150 from becoming damaged by a bio-stimulating signal. Thus, the first and second switch circuits 130 and 140 are set to be turned on when the bio-stimulating signal is generated. On the contrary, the first and second switch circuits 130 and 140 should not operate in the case where a bio-signal is provided through the bio-signal electrode 120. That is, the bio-signal needs not to be provided to the bio-signal measuring circuit 150 through a voltage divider. The reason is that the bio-signal is small in amplitude. Therefore, the first reference voltage Vref1 may be set to be greater than the voltage level of the bio-signal. The second reference voltage Vref2 may be set to be lower than the voltage level of the bio-signal.

For example, the bio-stimulating signal and the bio-signal may always have a negative voltage level. In this case, the first and second reference voltages Vref1 and Vref2 would be a negative voltage level. The bio-stimulating signal and the bio-signal may always have a positive voltage level. In this case, the first and second reference voltages Vref1 and Vref2 would be a positive voltage level. Alternatively, the bio-stimulating signal and the bio-signal may have a negative voltage level or positive voltage level. In this case, the first reference voltage Vref1 may have a positive voltage level and the second reference voltage Vref2 may have a negative voltage level.

Referring back to FIG. 1, the bio-signal measuring circuit 150 is connected to the first and second resistors R1 and R2 through the second node N2. The bio-signal measuring circuit 150 measures a voltage of the second node N2 in a bio-stimulating mode. In the bio-stimulating mode, the voltage of the second node N2 is a voltage generated when the bio-stimulating signal is divided by a voltage divider. Also, the bio-signal measuring circuit 150 may measure the bio-signal in a bio-signal measuring mode. In this case, the first and second switch circuits 130 and 140 are not turned on according to the above-described embodiment. Thus, a voltage of the second node N2 is the same as the voltage of the bio-signal. The bi-signal measuring circuit 150 may include all circuits that may measure the voltage or current signal. For example, the bio-signal measuring circuit 150 may include an analog digital converter (ADC), a comparator or an amplifier.

The bio-stimulating and bio-signal measuring circuit 100 in FIG. 1 is shown that each of components (the bio-stimulating signal generating circuit, the bio-signal electrode, the first and second switch circuits, or the like) include a single component. However, the present application is not limited thereto. Each component may include a plurality of components. For example, a set of the voltage divider that includes the first and second resistors R1 and R2, and the first and second switch circuits 130 and 140 may be in plurality. In this case, each set may be configured to operate under the individual condition. Also, although the first and second switch circuits 130 and 140 in FIG. 1 are shown to be configured as divided circuits, it is possible to configure them as a switch block that performs the same function. The above-described switch block would be capable of being implemented in hardware.

The operation of the bio-stimulating and bio-signal measuring circuit 100 is as follows. Firstly, the bio-stimulating signal generating circuit 110 generates a bio-stimulating signal in a bio-stimulating mode. The voltage signal is delivered to a user's body through the bio-signal electrode 120. Also, the voltage signal is delivered to the first and second switch circuits 130 and 140 through the first node N1. For example, the case where the voltage signal is greater than the first reference voltage Vref1 is assumed. In this case, the first switch circuit 130 is turned on. Subsequently, the first and second resistors R1 and R2 operates as a voltage divider. Thus, the voltage of the first node N1 is divided by the resistance ratio of the first and second resistors R1 and R2 and provided to the second node N2. Then, the bio-signal measuring circuit 150 measures a voltage of the second node N2.

Alternatively, in the case where the voltage signal of the first node N1 is lower than the second reference voltage Vref2, the second switch circuit 140 is turned on. The following operation is the same above. That is, the second switch circuit 140 is turned on so that the first and second resistors R1 and R2 operate as a voltage divider. Subsequently, the voltage of the bio-stimulating signal is divided and provided to the second node N2. As described above, the voltage value of the second node N2 would be within a range of input of the bio-signal measuring circuit 150. Thus, damage to the bio-signal measuring circuit 150 by the bio-stimulating signal that has an excessive voltage level is prevented. The bio-signal measuring circuit 150 may measure the voltage of the second node N2 divided by a voltage divider to monitor the actual voltage level of the bio-stimulating signal.

In a bio-signal measuring mode, the operation of the bio-stimulating and bio-signal measuring circuit 100 is as follows. The bio-signal electrode 120 receives the bio-signal from a user's body. In comparison to the bio-stimulating signal, the bio-signal has a relatively low voltage level. That is, the bio-signal is lower than the first reference voltage Vref1 and higher than the second reference voltage Vref2. Thus, the first and second switch circuits 130 and 140 are not turned by the bio-signal. That is, the voltage of the bio-signal is not divided through the first and second resistors R1 and R2. Subsequently, the bio-signal is provided to the bio-signal measuring circuit 150 through the first node N1 and the first resistor R1. The bio-signal measuring circuit 150 measures the received bio-signal.

In summary, the bio-stimulating and bio-signal measuring circuit 100 automatically lowers the voltage level of a signal by a voltage divider in the bio-stimulating mode to prevent damage to the bio-signal measuring circuit 150. In a bio-signal measuring mode, the bio-stimulating and bio-signal measuring circuit 100 also inactivates a voltage divider to measure the bio-signal as it is. Thus, the bio-stimulating and bio-signal measuring circuit 100 according to an embodiment of the present application may simultaneously perform bio-stimulating and bio-signal measurement by a single circuit without dividing the bio-signal electrode 120.

FIGS. 3 to 7 are circuit diagrams that show bio-stimulating and bio-signal measuring circuits according to other embodiments of the present application.

Figure 3:
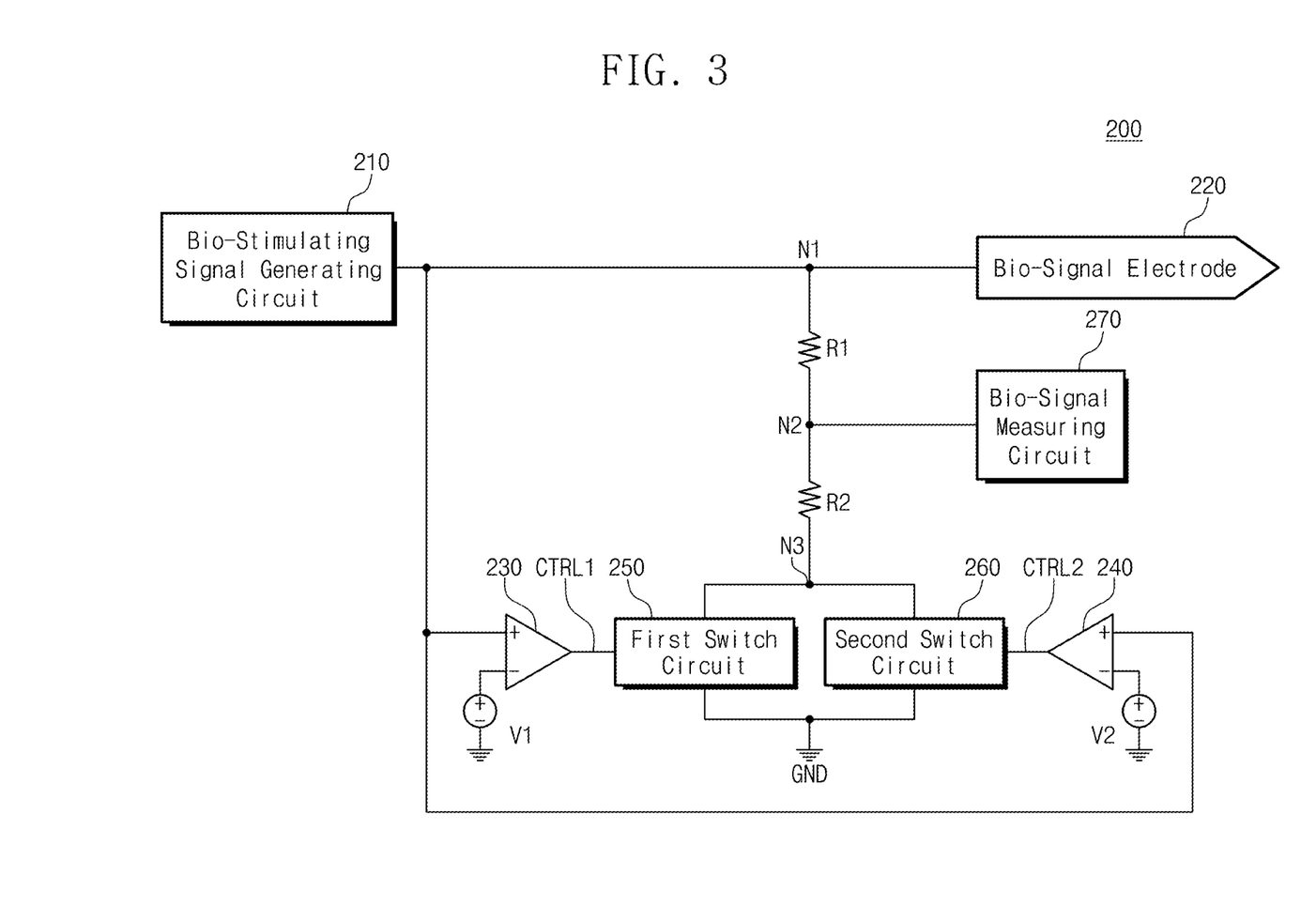
FIGS. 3 to 7 are circuit diagrams that show bio-stimulating and bio-signal measuring circuits according to other embodiments of the present application.

Referring to FIG. 3, a bio-stimulating and bio-signal measuring circuit 200 may include a bio-stimulating signal generating circuit 210, a bio-signal electrode 220, first and second resistors R1 and R2, first and second comparators 230 and 240, first and second voltage sources V1 and V2, first and second switch circuits 250 and 260, and a bio-signal measuring circuit 270. Except for the first and second comparators 230 and 240 and the first and second switch circuits 250 and 260, the bio-stimulating and bio-signal measuring circuit 200 in FIG. 3 has the same configuration and operation as the bio-stimulating and bio-signal measuring circuit 100 in FIG. 1. Thus, related descriptions are omitted.

The first comparator 230 is connected between the first node N1 and a node CTRL1. The first comparator 230 determines whether the voltage level of the first node N1 is greater than the voltage level of the first voltage source V1.

The first comparator 230 generates a turn-on voltage for the first switch 250 according to a result of determination. For example, the voltage level of the first voltage source V1 may be set to be equal to the first reference voltage Vref1 in FIG. 2.

The second comparator 240 is connected between the first node N1 and a node CTRL2. The second comparator 240 determines whether the voltage level of the first node N1 is lower than the voltage level of the second voltage source V2. The second comparator 240 generates a turn-on voltage for the second switch circuit 260 according to a result of determination. For example, the voltage level of the second voltage source V2 may be set to be equal to the second reference voltage Vref2 in FIG. 2.

The first and second switch circuits 130 and 140 in FIG. 1 are configured to be turned on by different reference voltages, respectively. In the case where the first switch circuit 130 is the NMOS transistor and the second switch circuit 140 is the PMOS transistor according to the above-described embodiment, the first and second reference voltages Vref1 and Vref2 become the threshold voltages of the NMOS transistor and the PMOS transistor, respectively. In this case, the threshold voltage may easily vary by a change in process voltage temperature (PVT). In an embodiment of FIG. 3, the first and second switch circuits 250 and 260 may use the same circuit. That is, the first and second comparators 230 and 240 generate the same turn-on voltage for respective nodes CTRL1 and CTRL2 according to a result of comparison. Also, the first and second voltage sources V1 and V2 may be configured as an adjustable, variable voltage sources. Thus, in comparison to the bio-stimulating and bio-signal measuring circuit 100 in FIG. 1, the bio-stimulating and bio-signal measuring circuit 200 in FIG. 3 is easy to set the voltage levels of the first and second voltage sources V1 and V2 to desired levels.

Figure 4:
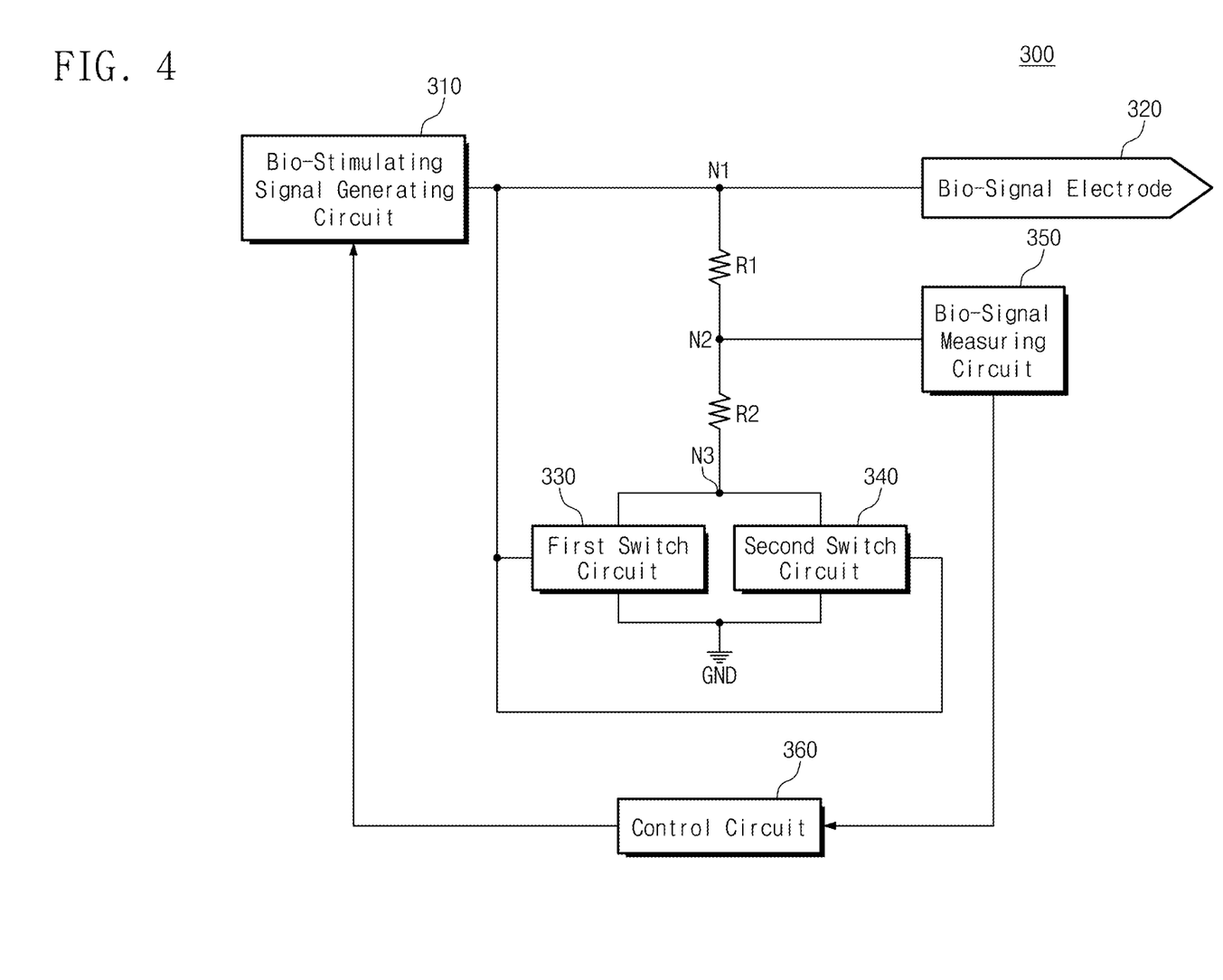

Referring to FIG. 4, the bio-stimulating and bio-signal measuring circuit 300 may include a bio-stimulating signal generating circuit 310, a bio-signal electrode 320, first and second resistors R1 and R2, first and second switch circuits 330 and 340, a bio-signal measuring circuit 350, and a control circuit 360. Except for the control circuit 360, the bio-stimulating and bio-signal measuring circuit 300 in FIG. 4 has the same configuration and operation as the bio-stimulating and bio-signal measuring circuit 100 in FIG. 1. Thus, related descriptions are omitted.

The control circuit 360 is connected to the bio-signal measuring circuit 350 and the bio-stimulating signal generating circuit 310. The control circuit 360 receives feedback on measurement values of a bio-stimulating signal and a bio-signal from the bio-signal measuring circuit 350. The control circuit 360 monitors the feedback measurement value to adjust the voltage level of a bio-stimulating signal generated by the bio-stimulating signal generating circuit 310. The reason for adjusting the voltage level of the bio-stimulating signal is that impedance varies according to the position of a user or the bio-signal electrode. In the case where bio-impedance varies, it is difficult to provide a desired waveform of the bio-stimulating signal for the same bio-stimulating signal. The control circuit 360 controls the bio-stimulating signal generating circuit 310 to provide the desired waveform of the bio-stimulating signal even when the bio-impedance varies.

For example, the control circuit 360 may include a processor, a micro processor, a micro controller, a central processing unit (CPU), a micro processing unit (MPU), a micro controlling unit (MCU) or the like.

For example, the control circuit 360 may include ADC and DAC. The ADC converts an analog signal monitored by the bio-signal measuring circuit 350 into a digital signal. The control circuit 360 generates a digital signal or code for controlling the bio-stimulating signal generating circuit 310 based on the digital signal from the ADC. The generated digital signal or code is converted into an analog signal by the DAC to control the bio-stimulating signal generating circuit 310 in real time.

As another example, the control circuit 360 may include a memory or interface circuit. The memory may store information, such as commands and programs for the operations of a bio-stimulating mode and a bio-signal measuring mode, data for bio-stimulation, and algorithms for the reading of a bio-signal. The memory may include a random access memory (RAM), a read only memory (ROM), an erasable programmable ROM (EPROM), an electrically EPROM (EEPROM), a flash memory or the like.

The interface circuit may relay the communication between a user and the control circuit 360 according to the control of the control circuit 360. As an example, the interface circuit may include an input interface, such as a keyboard, keypad, button, touch panel, touch screen, touch pad, touch ball, camera, microphone, gyroscope sensor, or vibration sensor. Also, the interface circuit may include an output interface, such as a liquid crystal display (LCD), organic light emitting diode (OLED) display device, active matrix OLED (AMOLED) display device, LED, speaker, or monitor.

Figure 5:
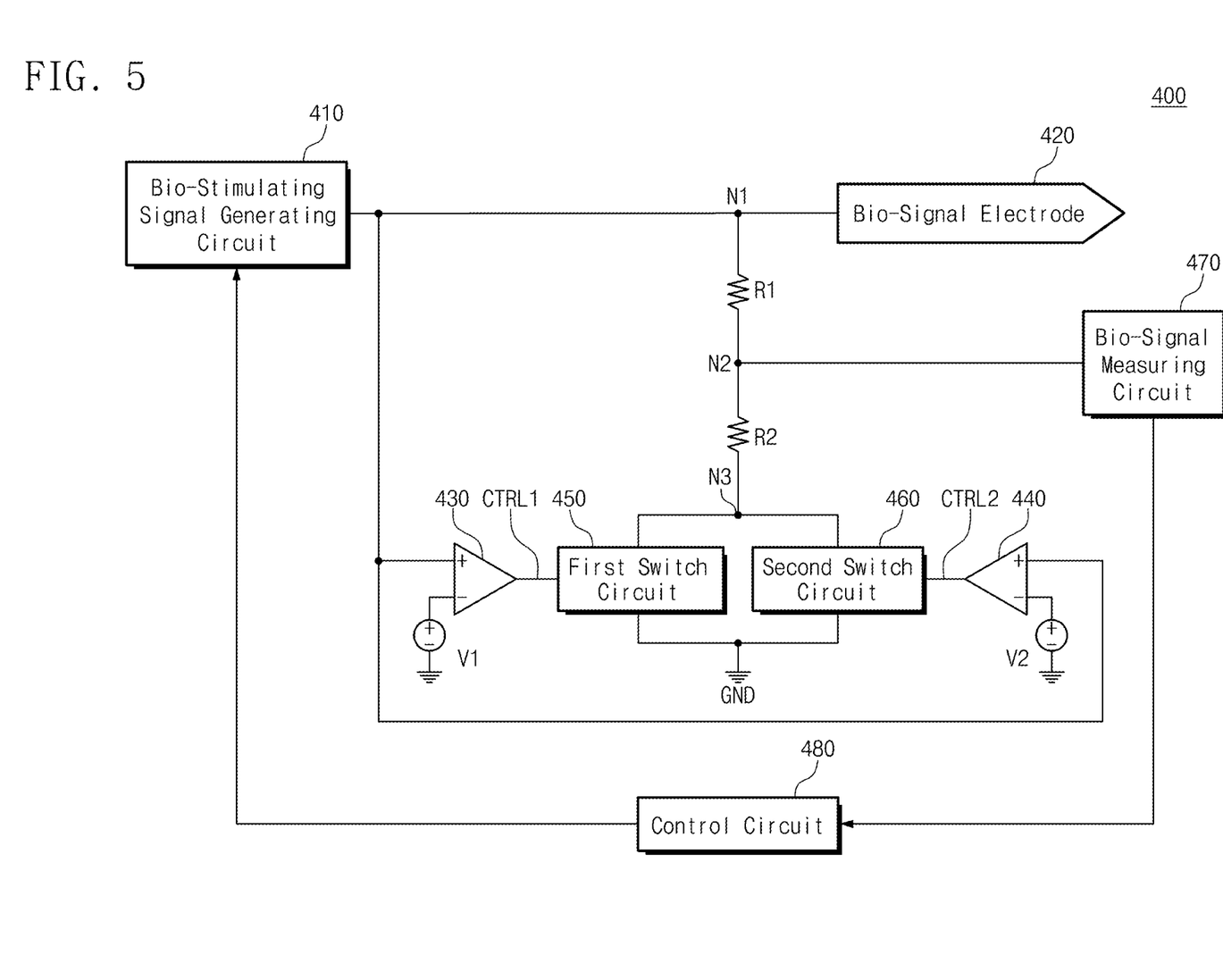

Referring to FIG. 5, a bio-stimulating and bio-signal measuring circuit 400 may include a bio-stimulating signal generating circuit 410, a bio-signal electrode 420, first and second resistors R1 and R2, first and second comparators 430 and 440, first and second voltage sources V1 and V2, first and second switch circuits 450 and 460, a bio-signal measuring circuit 470, and a control circuit 480. Except for the control circuit 480, the bio-stimulating and bio-signal measuring circuit 400 in FIG. 5 has the same configuration and operation as the bio-stimulating and bio-signal measuring circuit 200 in FIG. 3. Also, the control circuit 480 in FIG. 5 has the same configuration and operation of the control circuit 360 shown in FIG. 4. Thus, related descriptions are omitted.

Figure 6:
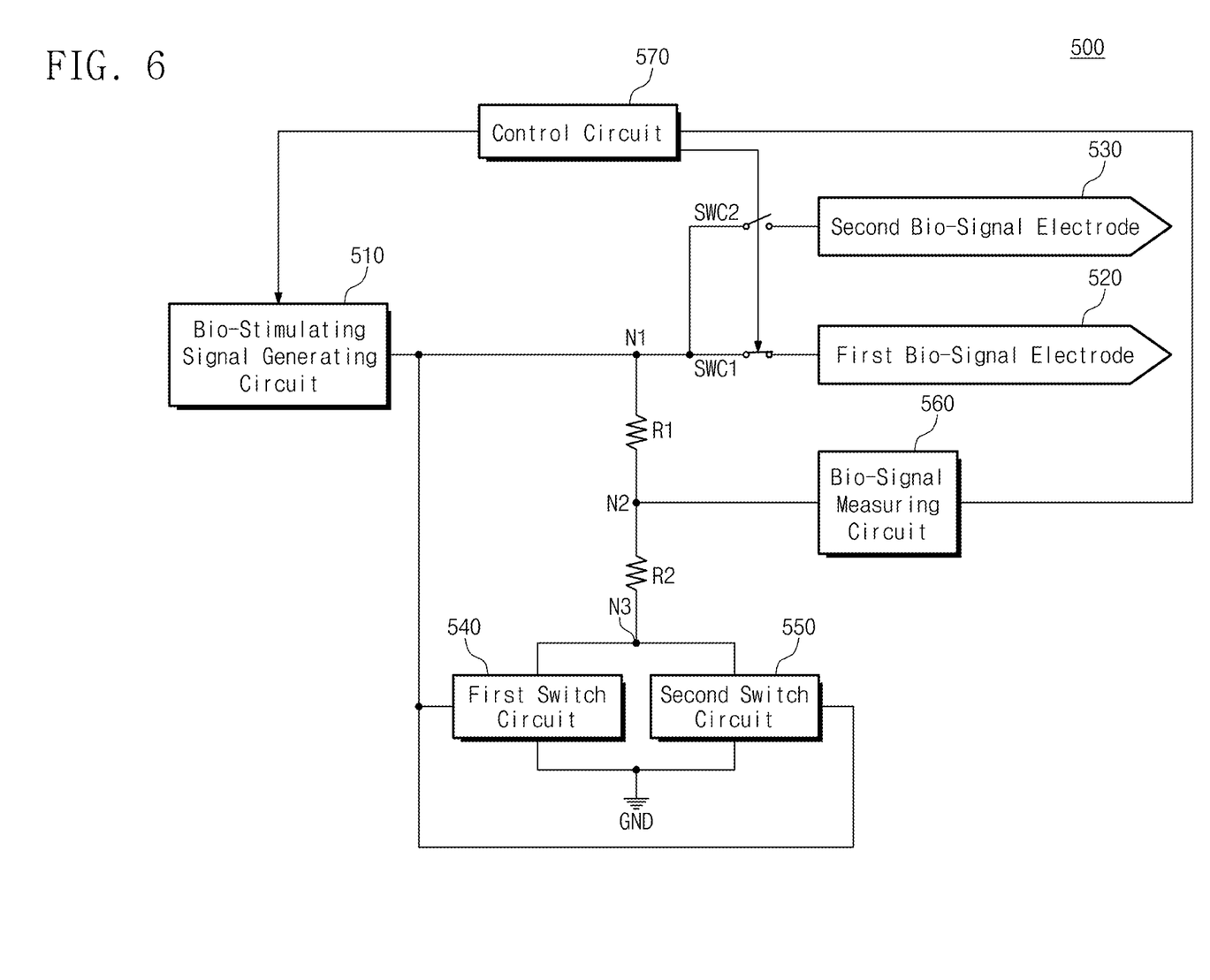

Referring to FIG. 6, the bio-stimulating and bio-signal measuring circuit 500 may include a bio-stimulating signal generating circuit 510, first and second bio-signal electrodes 520 and 530, first and second control switches SWC1 and SWC2, first and second resistors R1 and R2, first and second switch circuits 540 and 550, a bio-signal measuring circuit 560, and a control circuit 570. Except for the first and second bio-signal electrodes 520 and 530 and the first and second control switches SWC1 and SWC2, the bio-stimulating and bio-signal measuring circuit 500 in FIG. 6 has the same configuration and operation as the bio-stimulating and bio-signal measuring circuit 300 in FIG. 4. Thus, related descriptions are omitted.

The first bio-signal electrode 520 is connected to the first control switch SWC1. The first control switch SWC1 connects the first node N1 to the first bio-signal electrode 520 and is controlled by the control circuit 570. The second bio-signal electrode 530 is connected to the second control switch SWC2. The second control switch SWC2 connects the first node N1 to the second bio-signal electrode 530 and is controlled by the control circuit 570.

The bio-stimulating and bio-signal measuring circuit 500 in FIG. 6 may insert the first and second bio-signal electrodes 520 and 530 into different parts of a user body, respectively. Then, the control circuit 570 may select one of the first and second bio-signal electrodes 520 and 530 for a desired part. For example, in the case where the first bio-signal electrode 520 is selected, the control circuit 570 closes the first control switch SWC1 and opens the second control switch SWC2. Accordingly, the bio-stimulating and bio-signal measuring circuit 500 may perform stimulation and measurement on a desired one of a plurality of body parts by a single circuit.

Referring to FIG. 6, the control switches SWC1 and SWC2 and the bio-signal electrodes 520 and 530 are shown as two components. However, the present application is not limited thereto. Thus, the control switches and the bio-signal electrodes may be configured as two or more components. Also, although the first and second control switches SWC1 and SWC2 in FIG. 6 are shown to be configured as divided circuits, it is possible to configure them as a multiplexer that performs the same function. The above-described multiplexer would be capable of being implemented in hardware.

Figure 7:
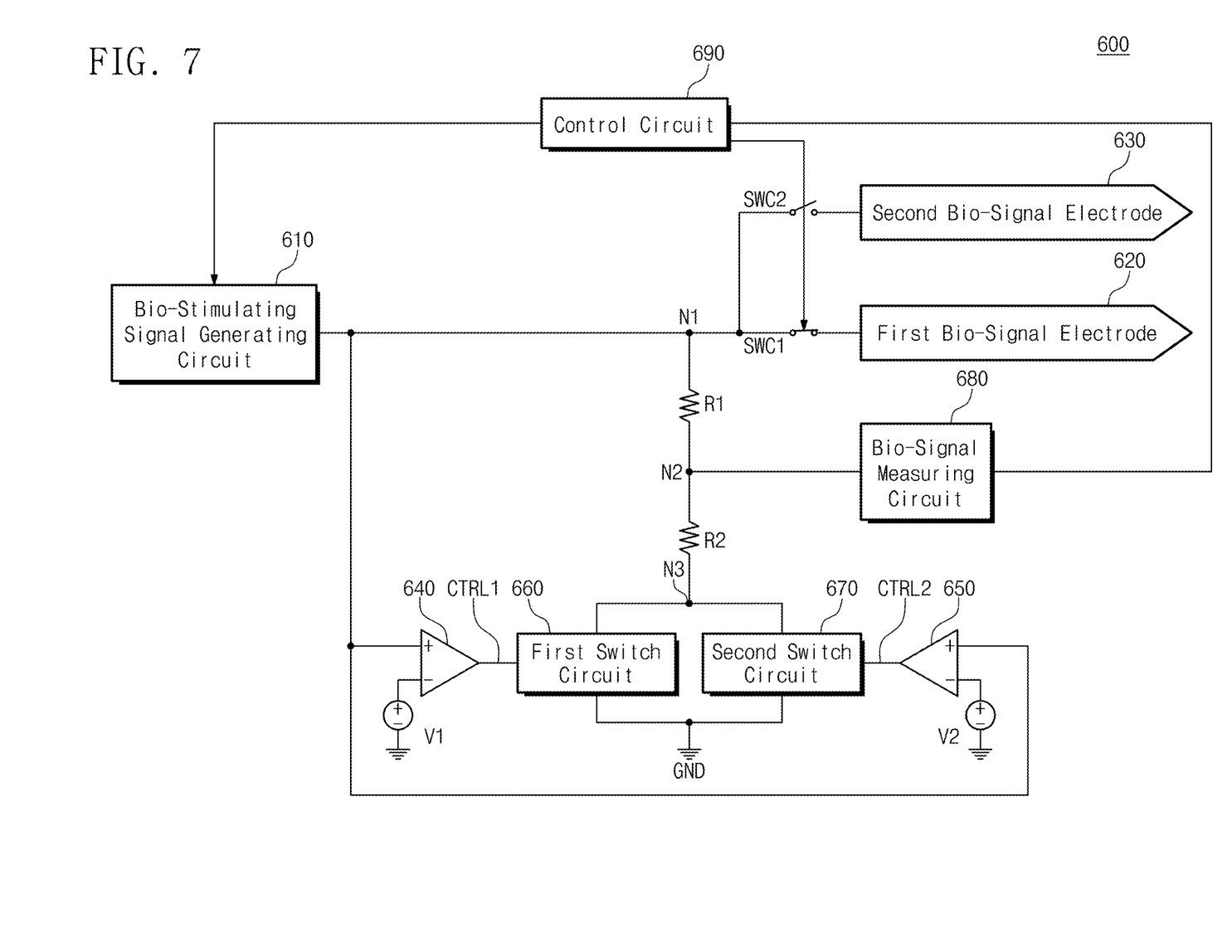

Referring to FIG. 7, a bio-stimulating and bio-signal measuring circuit 600 may include a bio-stimulating signal generating circuit 610, first and second bio-signal electrodes 620 and 630, first and second resistors R1 and R2, first and second comparators 640 and 650, first and second voltage sources V1 and V2, first and second switch circuits 660 and 670, a bio-signal measuring circuit 680, and a control circuit 690. Except for the first and second bio-signal electrodes 620 and 630 and the first and second control switches SWC1 and SWC2, the bio-stimulating and bio-signal measuring circuit 600 in FIG. 7 has the same configuration and operation as the bio-stimulating and bio-signal measuring circuit 400 in FIG. 5. Also, the first and second bio-signal electrodes 620 and 630 and the first and second control switches SWC1 and SWC2 shown in FIG. 7 have the same configurations and operations as the first and second bio-signal electrodes 520 and 530 and the first and second control switches SWC1 and SWC2 shown in FIG. 6. Thus, related descriptions are omitted.

The bio-stimulating and bio-signal measuring circuits 100 to 600 according to embodiments of the present application may be mounted by using a package, such as Package on Package (PoP), ball grid array (BGA), chip scale package (CSP), plastic leaded chip carrier (PLCC), Plastic Dual In-line Package (PDIP), Die in Waffle Pack, Die in Wafer Form, chip on board (COB), Ceramic Dual In-line Package (CERDIP), metric quad flat pack (MQFP), thin quad flat pack (TQFP), small outline integrated circuit (SOIC), shrink small outline package (SSOP), thin small outline package (TSOP), system in package (SIP), multi chip package (MCP), Wafer-level Fabricated Package (WFP), or Wafer-Level Processed Stack Package (WSP).

According to an embodiment of the inventive concept, the bio-stimulating and bio-signal measuring circuit may measure a bio-stimulating signal and a bio-signal by a single bio-electrode. Thus, a size of a circuit decreases and user convenience increases. Also, the bio-stimulating and bio-signal measuring circuit may simultaneously perform bio-stimulating and bio-signal measurement. Thus, the bio-stimulating and bio-signal measuring circuit may detect and handle an abnormal signal by real-time control.

As above, best embodiments are set forth in the drawings and in the specification. Although specific terms are used herein, they are only used for the purpose of describing the inventive concept and not used to define the meaning or limit the scope of the inventive concept set forth in the following claims. Therefore, a person skilled in the art would understand that it is possible to implement various variations and other equivalent embodiments from the inventive concept. Thus, the true technical protective scope of the inventive concept would be defined by the technical spirit of the following claims.

What is claimed is:

1. A circuit for measuring a bio-stimulating signal and a bio-signal, the circuit comprising:
   a bio-stimulating signal generating circuit configured to generate the bio-stimulating signal and deliver the bio-stimulating signal to a first node when the circuit is in a bio-stimulating mode;
   first and second bio-signal electrodes coupled to a multiplexer and configured to:
      receive the bio-stimulating signal from the first node when the circuit is in the bio-stimulating mode, and
      provide the bio-signal to the first node when the circuit is in a bio-signal measuring mode;
   the multiplexer coupled to the first node and configured to:
      select at least one of the first and second bio-signal electrodes in response to a control signal, and
      connect the selected bio-signal electrode to the bio-stimulating signal generating circuit;
   a first resistor coupled between the first node and a second node;
   a second resistor coupled between the second node and a switch block;
   the switch block coupled between a ground and the second resistor and configured to turn on when a voltage of the bio-stimulating signal is greater than a first reference voltage or lower than a second reference voltage and to turn off when the voltage of the bio-stimulating signal is greater than the second reference voltage;
   wherein the first and second resistors operate to divide a voltage of the first node to produce a voltage of the second node when the switch block is turned on and do not operate to divide the voltage of the first node when the switch block is turned off; and
   a bio-signal measuring circuit configured to measure the voltage of the second node,
   wherein the first reference voltage is greater than the second reference voltage.

2. The circuit of claim 1, further comprising a control circuit configured to receive feedback on a result of measurement from the bio-signal measuring circuit to adjust an intensity of the bio-stimulating signal, and generate the control signal.

3. The circuit of claim 1, wherein the switch block comprises:
   a first switch circuit configured to turn on when the bio-stimulating signal is greater than the first reference voltage; and
   a second switch circuit connected in parallel to the first switch circuit, and configured to turn on when the bio-stimulating signal is lower than the second reference voltage.

4. The circuit of claim 1, further comprising:
   a first comparator configured to determine whether the bio-stimulating signal is greater than the first reference voltage and generate a first turn-on voltage when the bio-stimulating signal is greater than the first reference voltage; and
   a second comparator configured to determine whether the bio-stimulating signal is lower than the second reference voltage and generate a second turn-on voltage when the bio-stimulating signal is lower than the second reference voltage, wherein the switch block comprises:
- a first switch circuit configured to be turned on by the first turn-on voltage; and
- a second switch circuit connected in parallel to the first switch circuit, and configured to be turned on by the second turn-on voltage.

5. The circuit of claim 4, further comprising a control circuit configured to receive feedback on a result of measurement from the bio-signal measuring circuit to adjust an intensity of the bio-stimulating signal, and generate the control signal.

* * * * *